(12) United States Patent
Gui et al.

(10) Patent No.: US 12,282,037 B2
(45) Date of Patent: Apr. 22, 2025

(54) AUTOMATIC AND RAPID DETECTION METHOD OF GRADATION FOR ASPHALT MIXTURE AND AUTOMATIC DETECTION DEVICE

(71) Applicant: Shaanxi Zhonglin Asphalt Pavement Maintenance Technology Co., Ltd, Xi'an (CN)

(72) Inventors: Xue Gui, Xi'an (CN); Dengcheng Ma, Xi'an (CN); Zhang Gui, Xi'an (CN); Hanwan Jiang, Xi'an (CN); Xinyao Li, Xi'an (CN); Gang Fang, Xi'an (CN); Yunxiang Wang, Xi'an (CN); Zexin Liu, Xi'an (CN); Qunde Li, Xi'an (CN); Jinbo Liu, Xi'an (CN); Nian Feng, Xi'an (CN); Ruihua Zhao, Xi'an (CN); Meng Liu, Xi'an (CN)

(73) Assignee: Shaanxi Zhonglin Asphalt Pavement Maintenance Technology Co., Ltd, Xi'an (CN)

(*) Notice: Subject to any disclaimer, the term of this patent is extended or adjusted under 35 U.S.C. 154(b) by 0 days.

(21) Appl. No.: 18/402,525

(22) Filed: Jan. 2, 2024

(65) Prior Publication Data
US 2024/0280452 A1    Aug. 22, 2024

(30) Foreign Application Priority Data

Feb. 16, 2023  (CN) .......................... 202310121142.2
Feb. 16, 2023  (CN) .......................... 202320225918.0

(51) Int. Cl.
*G01N 5/00*    (2006.01)
*G01N 1/40*    (2006.01)
(Continued)

(52) U.S. Cl.
CPC ............. *G01N 5/00* (2013.01); *G01N 1/4022* (2013.01); *G01N 1/4077* (2013.01); *G01N 1/44* (2013.01); *G01N 33/42* (2013.01)

(58) Field of Classification Search
CPC .......... G01N 5/00; G01N 1/4022; G01N 1/44; G01N 33/42; B07B 1/282; B07B 1/38
(Continued)

(56) References Cited

U.S. PATENT DOCUMENTS

| 10,024,771 B2 * | 7/2018 | Costonis | .................... B07B 1/38 |
| 2012/0263007 A1 * | 10/2012 | Swanson | ................. E01C 19/05 |
| | | | 366/22 |

* cited by examiner

*Primary Examiner* — Michael McCullough
*Assistant Examiner* — Jessica L Burkman
(74) *Attorney, Agent, or Firm* — Hemisphere Law, PLLC; Zhigang Ma

(57) ABSTRACT

An automatic and rapid detection method of a gradation for an asphalt mixture and an automatic device are provided. The method includes: asphalt mixture introduction; asphalt mixture dehydration, including: heating the asphalt mixture and dehydrating to a target dehydration rate; asphalt combustion, including: burning the asphalt mixture by using a combustion method to form smoke to be removed, thereby obtaining aggregates, and obtaining an asphalt content; aggregate screening, including: grading through screening the aggregates according to different particle sizes by using a vibration screening device, and then weighing the aggregates, thereby obtaining weights of the aggregates; and obtaining the gradation, including: calculating the gradation for the asphalt mixture according to the weights of the aggregates with the different particle sizes and the asphalt content. The method is operated by using simple instruments, automatically detecting moisture content, asphalt content, and aggregate gradation and rapidly detecting a new asphalt mixture.

10 Claims, 7 Drawing Sheets

(51) Int. Cl.
  *G01N 1/44* (2006.01)
  *G01N 33/42* (2006.01)
(58) Field of Classification Search
  USPC .............................................................. 209/3
  See application file for complete search history.

AUTOMATIC AND RAPID DETECTION METHOD OF GRADATION FOR ASPHALT MIXTURE AND AUTOMATIC DETECTION DEVICE

TECHNICAL FIELD

The disclosure relates to the technical field of asphalt pavement maintenance and gradation measurement of asphalt mixture, particularly to an automatic and rapid detection method of a gradation for an asphalt mixture and an automatic detection device for the asphalt mixture.

BACKGROUND

At present, recycling technology is used to treat waste asphalt mixture. Commonly used technical methods include hot recycling technology and cold recycling technology. At the same time, according to different sites of waste asphalt mixture recycling, it is divided into in-place recycling technology and on-site recycling technology. Therefore, it is necessary to first test contents and properties of each composition of the waste asphalt mixture. The detection of the waste asphalt mixture mainly includes determination of moisture content, determination of asphalt content, and measurement of aggregate gradation.

Nowadays, a commonly used method for determining the moisture content of asphalt mixture is to put the asphalt mixture into an oven for drying and heating to a constant weight, and then determine the moisture content of the asphalt mixture by a weight difference before and after drying and heating; a commonly used combustion method for determining the asphalt content is to put the asphalt mixture to be tested into an asphalt content tester, burn the asphalt through heat emitted by an electric heating element in the tester, and then use an electronic scale to weigh aggregates obtained after the combustion to measure the asphalt content; and a commonly used method for measuring the aggregate gradation is to place the burnt aggregates in a ceramic tray to cool down to room temperature, and then place the cooled aggregates on a standard screen frame, multiple layers of standard sieves of which form a set of sieves. The set of sieves is fixed on a vibration shaker to screen the aggregates, and finally the screened aggregates with different particle sizes are weighed to obtain the aggregate gradation. However, in the related art, detection on the waste asphalt mixture is carried out through manual operation to determine the moisture content, the asphalt content, and the aggregate gradation of the asphalt mixture step by step, which cannot achieve automatic detection. At the same time, the manual operation is complex and cumbersome, and a time for the detection time is longer, making it difficult to timely feedback detection results to an asphalt mixing station.

SUMMARY

In order to overcome the shortcomings of existing technologies, the disclosure provides an automatic and rapid detection method (also referred as to an automatic detection method) of a gradation for an asphalt mixture and an automatic detection device. Moreover, the disclosure realizes an integrated detection according to a top-down order, and combines technologies of computer control and sensor with the detection to achieve the automatic detection. Furthermore, the disclosure realizes real time detection of moisture content, asphalt content, and aggregate gradation of the asphalt mixture, which can replace the detection method realized by manual operation instruments. At the same time, the disclosure can provide gradation data of the asphalt mixture for the asphalt recycling mixing station, so as to accurately control an addition of new materials and intelligently control the asphalt recycling mixing station, ensuring a quality of reclaimed asphalt pavement (RAP).

The disclosure is realized by the following technical solution.

Specially, the disclosure provides an automatic and rapid detection method of a gradation for an asphalt mixture and an automatic detection device. The detection method includes the following steps:

asphalt mixture introduction, including: introducing the asphalt mixture by using a feeding mechanism;

asphalt mixture dehydration, including: heating the asphalt mixture in a heating device to remove moisture in the asphalt mixture and dehydrating the asphalt mixture to a target dehydration rate, thereby obtaining a dehydrated asphalt mixture;

asphalt combustion, including: burning the dehydrated asphalt mixture in a combustion device by using a combustion method to form smoke configured to be removed, thereby obtaining aggregates after the asphalt combustion, and obtaining an asphalt content by using a weight difference of the dehydrated asphalt mixture before and after the asphalt combustion;

aggregate screening, including: grading through screening the aggregates obtained after the asphalt combustion according to different particle sizes of the aggregates by using a vibration screening device, and then weighing the aggregates with the different particle sizes, thereby obtaining weights of the aggregates with the different particle sizes; and obtaining the gradation, including: calculating the gradation for the asphalt mixture according to the weights of the aggregates with the different particle sizes and the asphalt content.

According to the foregoing technical solution of the disclosure, by using different methods, the weights of the asphalt and the aggregates with the different particle sizes are respectively weighed, so that the weight of the asphalt and the weights of the aggregates with the different particle sizes can be obtained, thereby obtaining the asphalt content and the aggregate gradation of the asphalt mixture according to the obtained weights. Therefore, the disclosure realizes effects of rapid detection, simple operation, and short detection time.

In the foregoing technical solution, the asphalt combustion is directly performed in a high-temperature environment by burning the asphalt mixture to generate water, carbon dioxide and other gases, thereby achieving an extraction of the asphalt, and facilitating the calculation of the asphalt content according to the weight difference.

In the foregoing technical solution, automatic grading is performed according to the different particle sizes of the aggregates, thereby achieving automatic screening, improving working efficiency, and simplifying the whole detection process for the asphalt mixture.

In an embodiment of the disclosure, in the asphalt mixture dehydration, the asphalt mixture is heated to a temperature of 105 degrees Celsius (C) ±2° C. until the asphalt mixture is completely dehydrated.

In the foregoing technical solution, a temperature for the heating dehydration needs to reach 100° C. or above; and according to a moisture content determination test of the asphalt mixture by using an oven drying method, the temperature during the heating process in the disclosure is determined as 105±2° C. Moreover, according to the above requirements and actual needs, the asphalt mixture needs to be completely dehydrated (also referred as to the target dehydration rate, i.e., the moisture content being 0), which fully utilizes differences in gasification and combustion temperature between the moisture and other mixtures, and then the moisture is firstly removed, and then the gradation for the asphalt mixture can be calculated. Otherwise, the residual moisture can greatly cause an error. In conclusion, when the temperature is set to be 105±2° C., the moisture can fully evaporate; and the setting of above 100° ° C. fully considers the complete evaporation of the moisture.

In an embodiment of the disclosure, in the dehydration, microwave heating is used for the heating, and the microwave heating can reach to a target temperature directly. Moreover, a speed for the microwave heating relates to power, so that the higher the power is, the faster the speed for the microwave heating is, usually not exceeding 20 seconds (s).

In an embodiment of the disclosure, after the asphalt mixture dehydration, the method further includes: collecting the dehydrated asphalt mixture, which is performed by gathering the dehydrated asphalt mixture into a feeding hopper by using a large-port feeding-in small-port discharging mode, thereby gathering the dehydrated asphalt mixture into the feeding hopper.

In the foregoing technical solution, the large-port feeding-in mode is utilized, so that the asphalt mixture with large and small particle sizes can enter the heating device as soon as possible; if a feed port has a small diameter, it is easy to block due to the fact that the asphalt is viscous at the high-temperature environment, thereby slowing down a feeding speed of the asphalt mixture; moreover, when the asphalt mixture flows out, due to the fact that the particles flow accompanied with the asphalt, there is no need for a large discharge port, and then the small-port discharging mode is selected.

In an embodiment of the disclosure, in the asphalt combustion, the asphalt combustion is performed by a combustion furnace, and the combustion furnace is heated to a temperature of 520° C.-540° C.

In the foregoing technical solution, the asphalt combustion for the asphalt mixture is performed in the combustion furnace with a high-temperature environment (i.e., 538° C.) until data of a weighing system disposed outside the combustion furnace is stable, and then the asphalt combustion is automatically stopped. In the above process, characteristics of the asphalt are fully utilized, and in combination with characteristics of the combustion furnace, the effect of high-temperature combustion is achieved, so that the asphalt can be burned completely.

In an embodiment of the disclosure, in the aggregate screening, the automatic grading is achieved by the vibration screening device; the vibration screening device is provided with multiple layers of vibration sieves therein from a top to a bottom of the vibration screening device; and screened particle sizes of the multiple layers of vibration sieves are decreased from the top to the bottom of the vibration screening device.

In the foregoing technical solution, by means of gravity, etc., the aggregates with large particle sizes are first selected in a manner of large first and then small, and then the aggregates with small particle sizes flow out through screen holes with large particle sizes of the vibration sieve by means of gravity; and the foregoing technical solution is pushed in sequence until the aggregates with minimum particle sizes appear finally. Generally, the asphalt mixture would have an approximate gradation, but portions of the different particle sizes cannot be evaluated, and the aggregate screening according to the disclosure can solve the above-mentioned problem.

In an embodiment of the disclosure, a trajectory of the aggregates passing through the multiple layers of vibration sieves is a parabolic motion under an action of a drive mechanism.

In the foregoing technical solution, the parabolic motion trajectory of the aggregates has a trend of movement in two directions: on the one hand, the aggregates are thrown upwards, and on the other hand, the aggregates moves forwards. The parabolic trajectory is compared with a linear trajectory, which has the advantage that a screening efficiency of the aggregates can be improved.

In an embodiment of the disclosure, ends of the multiple layers of vibration sieves of the vibration screening device are correspondingly provided with multiple discharge ports.

In the foregoing technical solution, the discharge ports are disposed at the ends of the vibration sieves, and then the aggregates are screened then to flow out through the discharge ports, thereby collecting the discharged aggregates.

In an embodiment of the disclosure, after the asphalt combustion, the method further includes: discharging the aggregates after the asphalt combustion, which is performed by opening a discharge port of the combustion device according to a motion of the aggregates while controlling to open the multiple discharge ports corresponding to the multiple layers of vibration sieves in sequence.

In the foregoing technical solution, according to a control relationship between opening the multiple discharge ports of different layers of vibration sieves and opening the discharge port of the combustion device, there is a certain linkage between aggregate discharge and the aggregate screening. Specially, the multiple discharge ports of different layers of vibration sieves can be opened sequentially.

In an embodiment of the disclosure, in the asphalt combustion, after the dehydrated asphalt mixture enters a feed-receiving plate of the combustion device, an open-close cover plate of the combustion device is present in a closed state to form an asphalt sealing chamber.

In the foregoing technical solution, in order to ensure better combustion for the asphalt mixture and prevent impurities from entering, etc., there is a need to form the asphalt sealing chamber.

In another technical solution of the disclosure, an automatic detection device for an asphalt mixture is provided, including:

a frame, including multiple assembly departments from a top to a bottom of the frame;

the feeding mechanism, being assembled on a top portion of the multiple assembly departments of the frame through a support frame;

the heating device, being in communication with the feeding mechanism;

the combustion device, being disposed on an assembly department of the multiple assembly departments below the heating device and connected to a discharge port of the heating device;

the vibration screening device, being disposed below the combustion device and being disposed on a bottom portion of the multiple assembly departments of the frame; and a weighing device, disposed at multiple discharge ports of the vibration screening device.

In the foregoing technical solution, the frame in the device is provided with the multiple assembly departments and corresponding spaces to assemble other devices inside, and at the same time, the frame has a function of support, which can support the other devices inside the frame and a flow of the asphalt mixture.

In the foregoing technical solution, the multiple devices cooperate with a controller to achieve an effect of the automatic detection.

In an embodiment of the disclosure, a discharge port of the feeding mechanism forms a guide portion; and the guide portion is disposed facing towards the heating device.

In the foregoing technical solution, the feeding mechanism is inclined to an angle, and the inclined angle together with gravity is utilized to accelerate the flow speed of the asphalt mixture.

In an embodiment of the disclosure, the heating device is a microwave heating device, a position of the frame facing towards the support frame defines an assembly cavity, and the microwave heating device is disposed in the assembly cavity.

In the foregoing technical solution, the temperature for the microwave heating is easy to control, and the assembly cavity is utilized to assemble the microwave heating device inside the frame, which fixes the microwave heating device in the frame stably.

In an embodiment of the disclosure, the microwave heating device includes a housing; and the housing of the microwave heating device is provided with a magnetron and a rectangular waveguide connected to the magnetron therein; and an opening of the rectangular waveguide is disposed downwards.

In the foregoing technical solution, the magnetron and the rectangular waveguide are used to emit microwaves for the heating process.

In an embodiment of the disclosure, the housing of the microwave heating device is provided with a heat-dissipating plate therein, and an opposite side of the heat-dissipating plate of the housing of the microwave heating device is provided with vent fans.

In the foregoing technical solution, the heat-dissipating plate and the vent fans are set to ensure good heat dissipation and ventilation while the microwave heating.

In an embodiment of the disclosure, the discharge port of the microwave heating device is disposed at a portion of the housing of the microwave heating device facing towards the combustion device, and an open-close cover plate is disposed at the discharge port of the microwave heating device and configured to close or open the discharge port of the microwave heating device.

In the foregoing technical solution, the open-close cover plate aims to control the flow of the asphalt mixture passing through the microwave heating device, and at the same time, the open-close cover plate aims to achieve sealing during the asphalt combustion.

In an embodiment of the disclosure, the combustion device is assembled with a ball screw thereon, the ball screw is provided with a slide block, and the slide block is fixedly connected to a fixed block extending from an end of the open-close cover plate of the microwave heating device.

In the foregoing technical solution, the slide block and the ball screw cooperate to realize automatic opening or closing of the open-close cover plate.

In an embodiment of the disclosure, a feed-receiving plate is disposed in the combustion device, the feed-receiving plate is fixedly connected to telescopic cylinders, and the telescopic cylinders are hinged to inner walls of the combustion device.

In the foregoing technical solution, the telescopic cylinders control a motion of the feed-receiving plate, achieving better feeding. Moreover, after the aggregate screening, a feed blocking door is disposed at the multiple discharge ports of the vibration screening device, and the feed blocking door is connected to the slide block through the fixed block.

In an embodiment of the disclosure, the combustion device is assembled on the frame through suspension rods and pulling sensors.

In the foregoing technical solution, a number of the suspension rods are multiple, the multiple suspension rods define chambers inside the frame, and the heating device and the combustion device are disposed in their respective chambers from a top to a bottom of the frame.

In an embodiment of the disclosure, the vibration screening device includes: a box body, a base configured to support the box body, and a vibration motor disposed at a bottom of the box body; and the box body is provided with multiple layers of vibration sieves therein.

In the foregoing technical solution, the multiple layers of vibration sieves are set, and then apertures of the multiple layers of vibration sieves are adjusted to screen the aggregates with the different particle sizes

DESCRIPTION OF REFERENCE NUMERALS

1—feeding mechanism;
2—microwave heating device; 21—magnetron; 22—rectangular waveguide; 23—vent fan; 24—telescopic cylinder; 25—arc-shaped feed-receiving plate; 26—heat-dissipating plate; 27—open-close cover plate; 28—ball screw slider assembly; 281—ball screw; 282—slide block; 29—feeding hopper;
3—combustion device; 31—flat feed-receiving plate; 32—heater; 33—filter chamber; 34—exhaust vent;
4—weighing system;

5—vibration screening device; 51—box body; 52—vibration motor; 53—upper cover; 54—vibration sieve; 55—base; 56—discharge port; 57—feed blocking door; 58—fixed block;
6—frame;
7—support frame;
8—suspension rod;
9—pulling sensor; and
10—weighing hopper.

DETAILED DESCRIPTION OF EMBODIMENTS

In order to make the objectives and technical solutions of the disclosure clearer and more convenient to be understood. The disclosure will be further described in detail below with reference to attached drawings and illustrated embodiments, and the illustrated embodiments described herein are merely used to explain the disclosure and are not intended to limit the disclosure.

In the description of the disclosure, it should be understood that orientations or positional relationships indicated by terms of "center", "longitudinal", "transverse", "upper", "lower", "front", "rear", "left", "right", "vertical", "horizontal", "top", "bottom", "inner", "outer", etc. are merely used to facilitate the description of the disclosure and to simplify the description, rather than to indicate or imply that a specific device or an element must possess a particular orientation, or be constructed and operated in a particular orientation. Therefore, the terms cannot be understood as a limitation to the disclosure. In addition, terms of "first" and "second" are used for descriptive purposes only and cannot be understood as indicating or implying relative importance or implicitly indicating the number of indicated technical features. Thus, the features defined with "first" and "second" may explicitly or implicitly include one or more of the defined features. In the description of the disclosure, unless otherwise stated, "multiple" means two or more. In the description of the disclosure, unless expressly specified and limited thereto, terms of "mounted", "connected to", and "connected with" should be understood broadly. For example, the connection may be a fixed connection, a detachable connection, or an integrated connection; may be a mechanical connection or an electrical connection; may be a direct connection or an indirect connection by means of an intermediate medium; and may be an internal communication between two elements. For those skilled in the related art, they can understand the specific meanings of the above terms in the disclosure.

Figure 1:
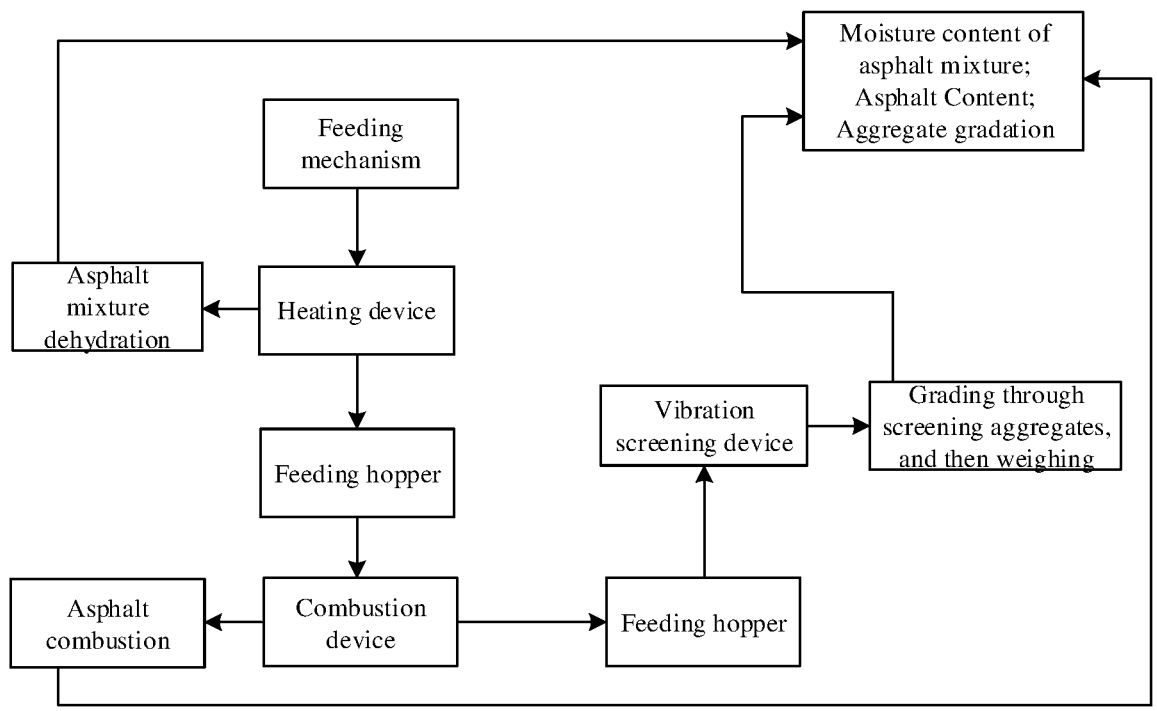
FIG. 1 illustrates a flowchart of an automatic and rapid detection method of a gradation for an asphalt mixture according to an embodiment of the disclosure.

With reference to FIG. 1, an embodiment of the disclosure provides an automatic and rapid detection method of a gradation for an asphalt mixture. As shown in FIGS. 2-8, an embodiment of the disclosure provides an automatic detection device for the asphalt mixture suitable for implementing the automatic and rapid detection method of the gradation for the asphalt mixture. Specially, the automatic detection device includes: a feeding mechanism 1 used for obtaining the asphalt mixture, a heating device used for dehydration such as a microwave heating device 2, a combustion device 3 used for asphalt combustion, weighing systems 4, and a vibration screening device 5 used for aggregate screening.

The asphalt mixture enters the automatic detection device through the feeding mechanism 1. Firstly, the asphalt mixture falls down on an arc-shaped feed-receiving plate 25 of the microwave heating device 2; moisture in the asphalt mixture is removed in the microwave heating device 2, and then the weighing system 4 determines a moisture content of the asphalt mixture. In an illustrated embodiment of the disclosure, the determination of moisture content can be as follows: first, weights of the asphalt mixture before and after the dehydration are measured through the weighing system 4, thereby obtaining a weight difference before and after heating; and then the moisture content of the asphalt mixture is calculated by using a moisture content formula (i.e., a ratio between the weight difference before and after heating to a weight of the asphalt mixture after being heated). In an illustrated embodiment of the disclosure, the asphalt mixture is heated to a temperature of 105 degrees Celsius (° C.) ±2° C. until the asphalt mixture is completely dehydrated. In the illustrated embodiment, a temperature for completing the dehydration needs to reach 100° C. or above; and according to a moisture content determination test of the asphalt mixture by using an oven drying method, the temperature during the heating process in the disclosure is determined as 105±2° C. Moreover, according to the above requirements and actual needs, the asphalt mixture needs to be completely dehydrated (i.e., the moisture content being 0), which fully utilizes differences in gasification and combustion temperature between the moisture and other mixtures, and then the moisture is firstly removed, and then the gradation for the asphalt mixture can be calculated. Otherwise, the residual moisture can greatly cause an error. In conclusion, when the temperature is set to be 105±2° C., the moisture can fully evaporate; and the setting of above 100° C. fully considers the complete evaporation of the moisture. Furthermore, microwave heating is used for the dehydration, which can directly reach a target temperature; and a microwave heating speed is related to power; and the higher the power is, the faster the heating speed is, usually not exceeding 20 seconds (s).

The asphalt mixture that has been dehydrated by the microwave heating is then fed into the combustion device 3 through a feeding hopper 29 of the microwaving heating device 2. Specifically, the dehydrated asphalt mixture can be gathered into the feeding hopper 29 by using a large-port feeding-in small-port discharging mode to collect the asphalt mixture. By using the large-port feeding-in mode, the asphalt mixture with different particle sizes can enter as soon as possible; and meanwhile due to viscosity of asphalt at a high temperature, if a diameter of the feed port is small, it is easy to cause blockage, which slows down the feeding speed of the asphalt mixture. However, when the asphalt mixture flows out, particle flow will drive a part of asphalt to flow out, there is no need for a large discharge port, and then the small-port discharging mode is selected. After sufficient combustion, the asphalt mixture is burned into smoke, and the smoke is discharged into air through the combustion device 3, i.e., a filter chamber 33 of the combustion device 3, thereafter weighing an asphalt content in the asphalt mixture by using the weighing system 4 disposed outside the combustion device 3. In an illustrated embodiment of the disclosure, the combustion device 3 is heated to a temperature of 520° C.-540° C. for asphalt combustion. The asphalt in the asphalt mixture is burned in a high-temperature environment of the combustion device 3 (e.g., at 538° C.) until data of the weighing system 4 disposed outside the combustion device 3 stabilizes, the asphalt combustion automatically stops. During the foregoing process, characteristics of the asphalt are fully utilized combined with characteristics of the combustion device 3, high-temperature combustion is realized, which ensures thorough combustion of the asphalt.

Aggregates obtained after the asphalt combustion are then fed into the vibration screening device 5 through a feeding hopper 29 of the combustion device 3. Within the vibration screening device 5, the aggregates are screened according to different particle sizes of the aggregates, and finally, the aggregates with different particle sizes can be weighed individually to obtain an aggregate gradation.

Figure 2:
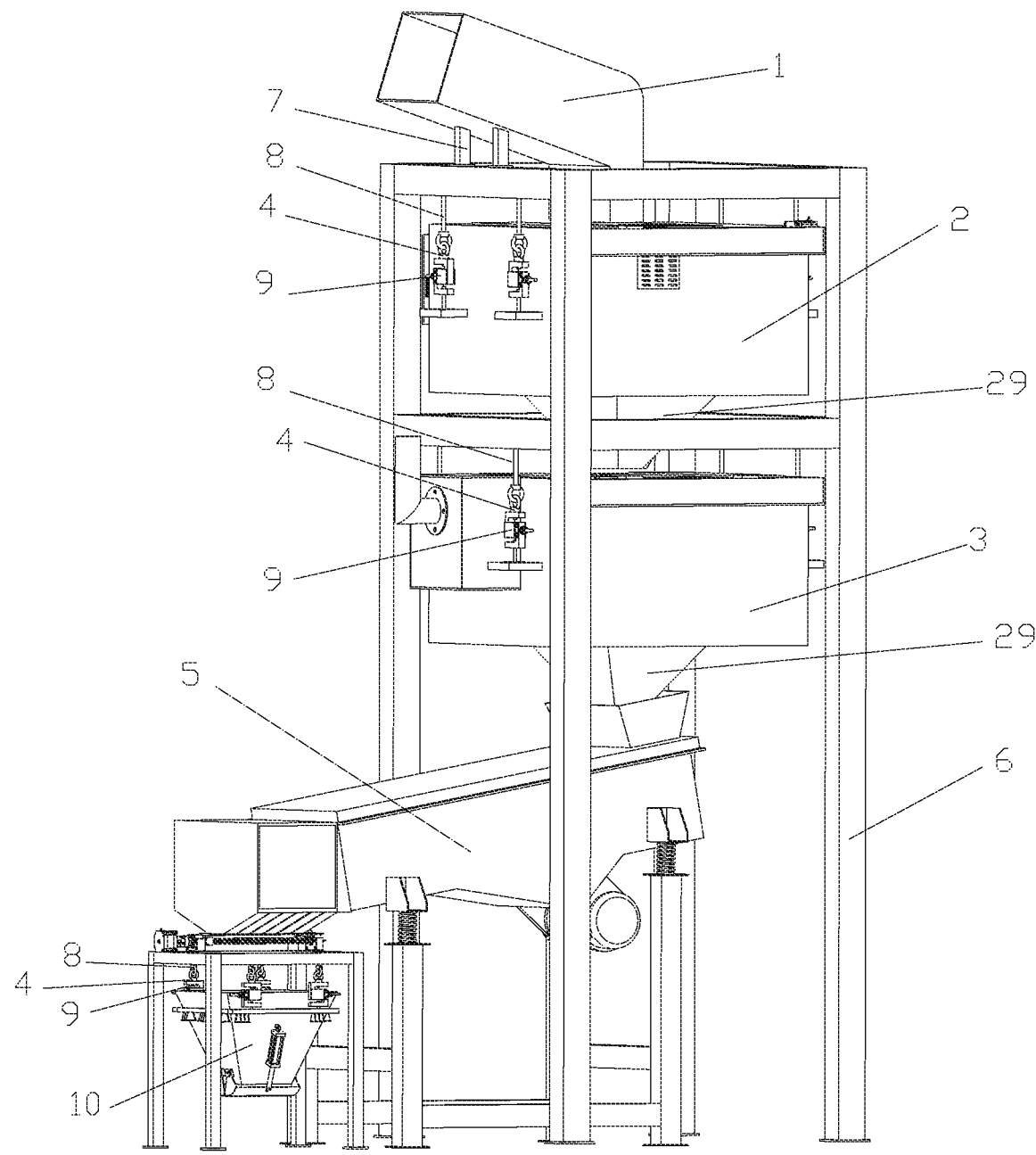
FIG. 2 illustrates a schematic structural diagram of an automatic detection device for an asphalt mixture according to an embodiment of the disclosure.

With reference to FIG. 2, the automatic detection device in the embodiment further includes a frame 6, a feeding mechanism 1 and a support frame 7 installed on the frame 6, the microwave heating device 2 disposed on an upper portion of the frame 6, and the vibration screening device 5 disposed on a bottom portion of the frame 6. Specially, the support frame 7 and the feeding mechanism 1 are disposed on a top portion of the frame 6; the microwave heating device 2 is connected to the frame 6 through suspension rods 8 and pulling sensors 9; and the vibration screening device 5 is not connected to the frame 6, i.e., the vibration screening device 5 is a linear vibration screen machine disposed on a horizontal plane as the same as the frame 6. A feed port of the vibration screening device 5 is aligned with a discharge port of the combustion device 3.

A middle portion of the frame 6 is connected with the combustion device 3, and the combustion device 3 is connected to the frame 6 through corresponding suspension rods 8 and pulling sensors 9. The vibration screening device 5 is installed in the bottom portion of the frame 6, and there is a weighing hopper 10 disposed at multiple discharge ports of the vibration screening device 5. The weighing hopper 10 is connected to a frame of the vibration screening device 5 through corresponding suspension rods 8 and pulling sensors 9, and the weighing hopper 10, the corresponding suspension rods 8, and the corresponding pulling sensors 9 together form a weighing device. In the embodiment of the disclosure, the weighing systems 4 (including the suspension rods 8 and the pulling sensors 9) are respectively installed on the corresponding device (i.e., the microwave heating device 2 and the combustion device 3) through the frame 6, and are both located at support points in half heights of the corresponding devices (referring to the connection mode of the weighing hopper 10). The weighing systems 4 are respectively installed outside the corresponding devices, and there are four pulling sensors 9 disposed outside each device. When the multiple pulling sensors 9 are installed at the same height, a center of gravity of the corresponding device is located below the support point, thereby placing the corresponding device more stable.

Figure 3:
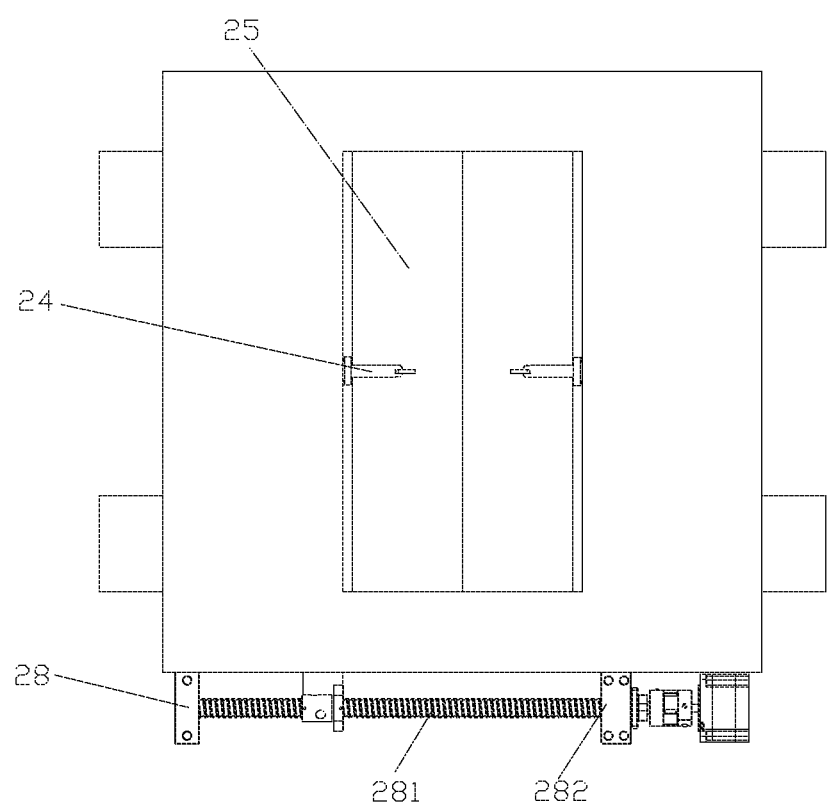
FIG. 3 illustrates a schematic structural diagram of a microwave heating device according to the embodiment of the disclosure.
Figure 4:
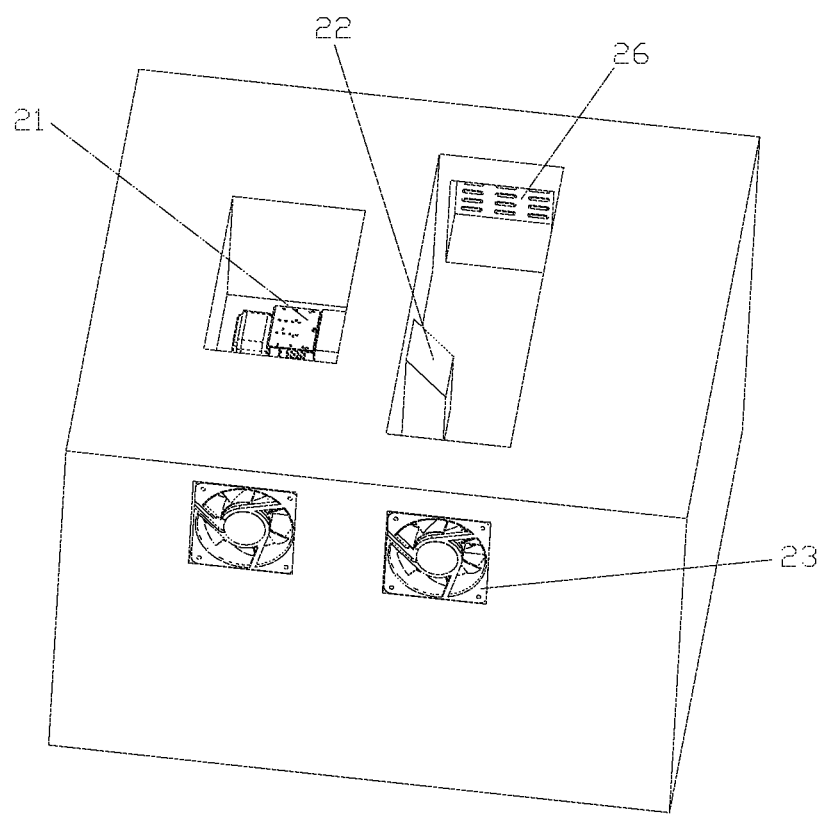
FIG. 4 illustrates another schematic structural diagram of the microwave heating device according to the embodiment of the disclosure.

As shown in FIGS. 2-4, the microwave heating device 2 is equipped with a magnetron 21, a rectangular waveguide 22, vent fans 23, telescopic cylinders 24, an arc-shaped feed-receiving plate 25, a heat-dissipating plate 26, an open-close cover plate (not shown in FIG. 3, please refer to the open-close cover plate 27 of the combustion device 3 in FIG. 5), a ball screw slider assembly 28, a feeding hopper 29, and other structures.

The support frame 7 is fixed at the top portion of the frame 6, and the feeding mechanism 1 is connected to the support frame 7, and the feeding mechanism 1 is installed above the support frame 7. An opening end (also referred as to a feed port) of the feeding mechanism 1 faces outward and is inclined upwards, and an outlet end (also referred as to a discharge port) of the feeding mechanism 1 is vertically downward. The microwave heating device 2 is connected to the top portion of the frame 6 through the suspension rods 8 that are disposed on two sides of a housing of the microwave heating device 2 and connected to the pulling sensors 9, respectively. A top portion of the housing of the microwave heating device 2 is equipped with the open-close cover plate 27, and the ball screw slider assembly 28 is fixed on an outer side of the housing of the microwave heating device 2. The ball screw slider assembly 28 includes a ball screw 281 and a slide block 282, and the slide block 282 is fixedly connected to the open-close cover plate 27.

Firstly, before the asphalt mixture enters, the slide block 282 installed on the microwave heating device 2 starts to move, driving the open-close cover plate 27 to open a heating feed port of the microwave heating device 2. The asphalt mixture enters the microwave heating device 2 through the feeding mechanism 1 and the heating feed port, and then falls on the arc-shaped feed-receiving plate 25 inside the housing of the microwave heating device 2. When the asphalt mixture falls onto the arc-shaped feed-receiving plate 25 completely, the slide block 282 moves back to the previously closed state, and a closed structure is formed inside the housing of the microwave heating device 2, which can effectively suppress microwave leakage.

An upper portion of the housing of the microwave heating device 2 is equipped with the magnetron 21, the rectangular waveguide 22, and the exhaust fans 23. Microwaves emitted by the magnetron 21 are transmitted downwards through the rectangular waveguide 22, and then absorbed by the asphalt mixture for being heated. Due to water being a polar molecule, most of the microwaves inside the housing are absorbed and heated by the water, and the water (also referred as to moisture content) in the asphalt mixture evaporates into water vapor. There are through holes disposed on two sides of the upper portion of the housing of the microwave heating device 2, and the heat-dissipating plate 26 is installed outside the through holes on a side of the two sides, and a ventilation waveguide panel is installed inside the heat-dissipating plate 26; and the exhaust fans 23 are disposed outside the through holes on the other side of the two sides, and ventilation waveguide panels are installed inside the exhaust fans 23. The exhaust fans 23 works to expel the water vapor from the inner chamber of the microwave heating device 2.

When the asphalt mixture enters the microwave heating device 2, the exhaust fans 23 start working; and the microwave dehydration and exhaust fan 23 working simultaneously occur. Therefore, when the dehydration is completed, the water vapor is also discharged outside the housing of the microwave heating device 2. At the same time, the pulling sensors 9 outside the housing of the microwave heating device 2 also synchronously measures the weight of the asphalt mixture at each moment, and a weight change of the asphalt mixture can be reflected by data change of the pulling sensors 9. The weighing process and the heating dehydration process are also carried out simultaneously, which can improve the efficiency and accuracy of weighing. The pulling sensors 9 can timely transmit the data to a controller.

After the dehydration is completed, the controller controls the telescopic cylinders 24 to move and open the arc-shaped feed-receiving plate 25. The arc-shaped feed-receiving plate 25 is designed to be open towards opposite directions. After receiving a command from the controller, the arc-shaped feed-receiving plate 25 opens for feeding. A heating discharge port of the microwave heating device 2 disposed on a bottom portion of the microwave heating device 2 is equipped with the feeding hopper 29, which has the same size as an inner cavity of the housing of the microwave heating device 2. The feeding hopper 29 of the microwave heating device 2 is disposed above the open-close cover plate 27 of the combustion device 3 and corresponds to a combustion feed port of the combustion device 3, and then the asphalt mixture passes through the feeding hopper 29 of the microwave heating device 2 and falls into the next device (i.e., the combustion device 3).

Figure 5:
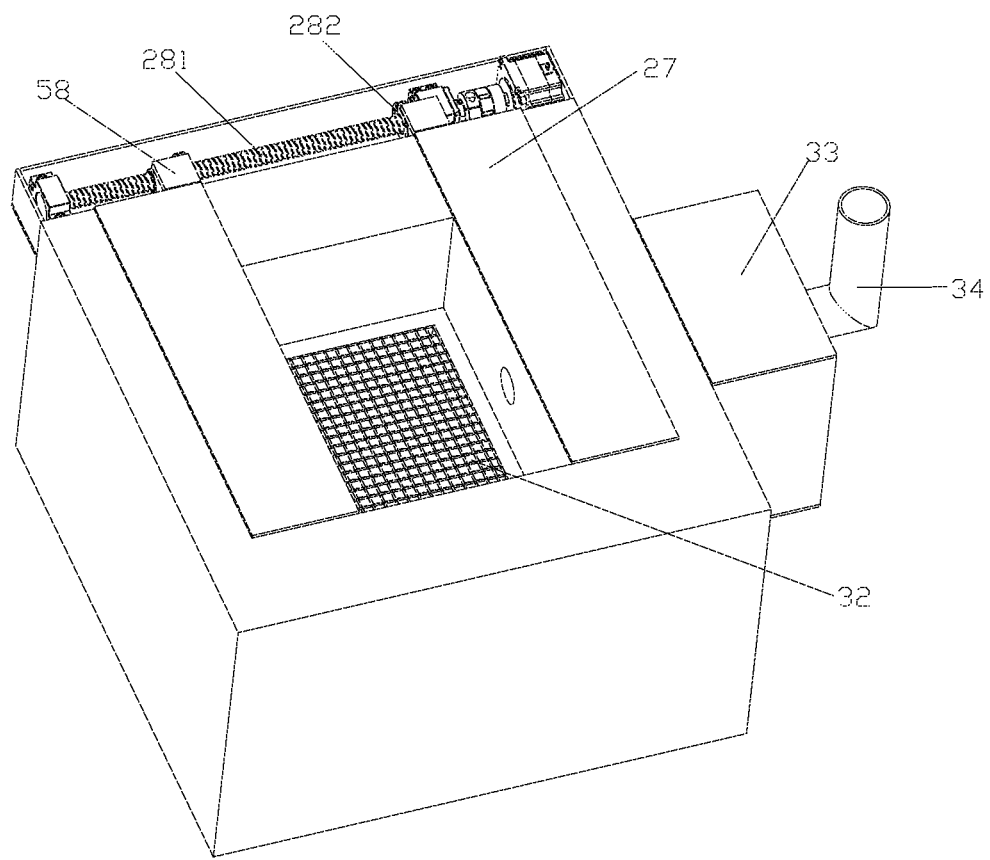
FIG. 5 illustrates a schematic structural diagram of a combustion device according to the embodiment of the disclosure.
Figure 7:
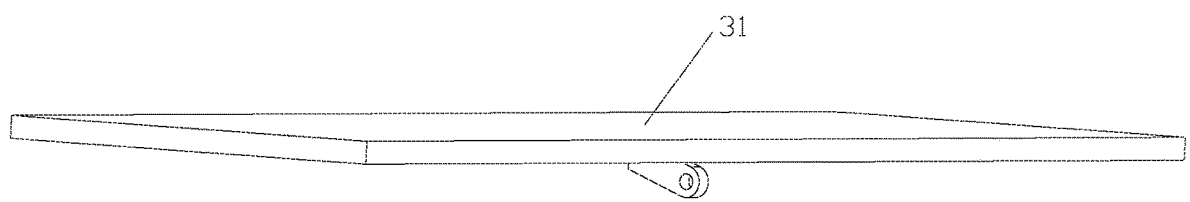
FIG. 7 is a schematic structural diagram of a flat feed-receiving plate according to the embodiment of the disclosure.
Figure 8:
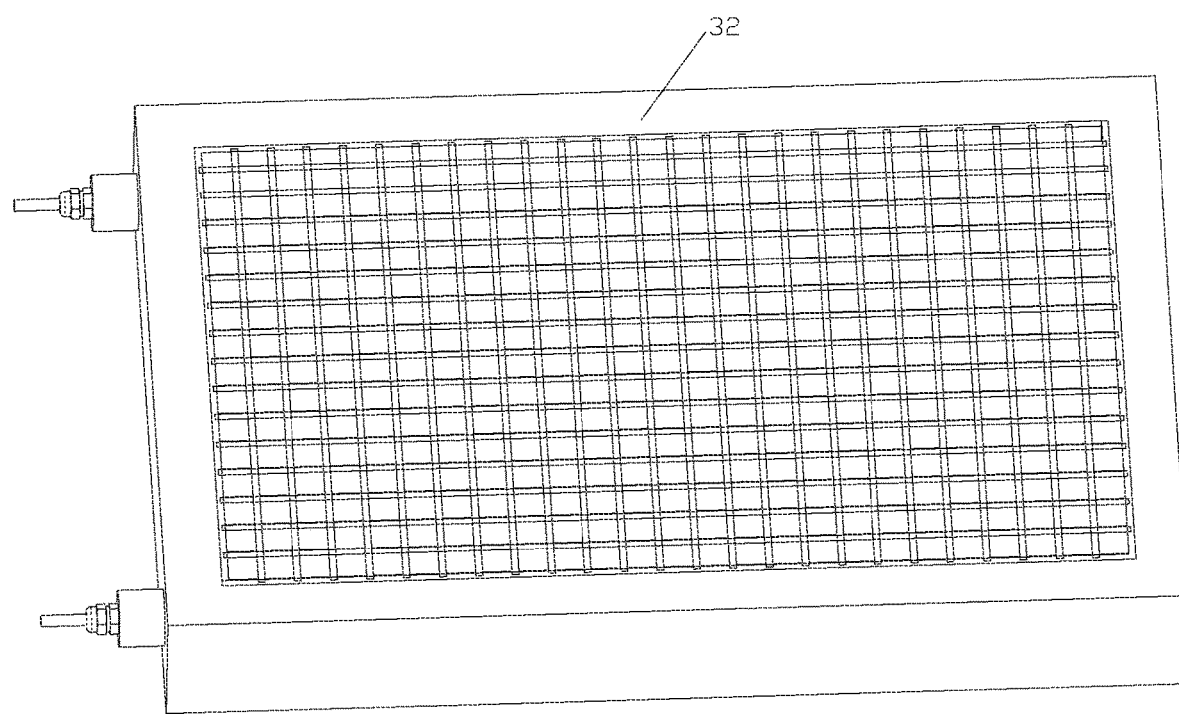
FIG. 8 is a schematic structural diagram of a heater according to the embodiment of the disclosure.

As shown in FIG. 5, FIG. 7, and FIG. 8, the combustion device 3 is equipped with a flat feed-receiving plate 31, a heater 32, a filter chamber 33, an exhaust vent 34, and telescopic cylinders (not shown in FIG. 5, please refer to the telescopic cylinders 24 in FIG. 3), and other structures.

The middle portion of the frame 6 is connected with the combustion device 3, and the combustion device 3 is connected to the frame 6 through the corresponding suspension rods 8 and the corresponding pulling sensors 9. A top portion of the combustion device 3 is equipped with an open-close cover plate 27, which is made of high-temperature insulation material. An outer side of a housing of the combustion device 3 is fixed with a ball screw slider assembly 28, which includes a ball screw 281 and a slide block 282. The slide block 282 is fixedly connected to the open-close cover plate 27 through a fixed block 58 (such as a portion extending from an end of the open-close cover plate 27).

In an illustrated embodiment of the disclosure, a linkage between the open-close cover plate 27 of the combustion device 3 and the fixed block 58 of the vibration screening device 5 is specially illustrated as follows.

Firstly, when the asphalt mixture completes the dehydration, the open-close cover plate 27 of the combustion device 3 is opened (i.e., the open-close cover plate 27 of the combustion device 3 being opened before the falling down asphalt mixture completes the dehydration), and then the completely dehydrated asphalt mixture quickly falls into the combustion device 3. The falling down asphalt mixture passes through the heater 32 and finally falls onto the flat feed-receiving plate 31 disposed attached to the heater 32. When the asphalt mixture completely falls into the combustion device 3, the controller controls the open-close cover plate 27 of the combustion device 3 to close. At this time, a closed inner chamber (also referred as to an asphalt sealing chamber) is formed inside the housing of the combustion device 3. Due to the combustion device 3 is preheated in advance, asphalt in the asphalt mixture is directly burned. When the weight in the combustion device 3 detected by the weighing system 4 disposed on the outer side of the housing of the combustion device 3 does not change, the flat feed-receiving plate 31 opens under the control of the controller, and the aggregates after the combustion directly falls into a feed port of the vibration screening device 5.

A basic working process mentioned above is as follows: the open-close cover plate 27 of the combustion device 3 is opened, the asphalt mixture falls down, and after the asphalt mixture completely falls into the combustion device 3, the open-close cover plate 27 is closed to form a closed structure (i.e., the closed inner chamber), and the asphalt mixture burns inside the combustion device 3. After the asphalt combustion is completed, the flat feed-receiving plate 31 is opened, and the aggregates obtained after the combustion falls down and enters the next process.

As mentioned above, after the microwave heating, the moisture in the asphalt mixture has been heated and evaporated, and then the asphalt mixture falls into the combustion device 3 through the feeding hopper 29 of the microwave heating device 2. Before the asphalt mixture enters the combustion device 3, the slide block 282 of the ball screw slider assembly 28 installed on the combustion device 3 starts to move to drive the open-close cover plate 27 to open the combustion feed port of the combustion device 3. Then, the asphalt mixture enters the combustion device 3, thereafter falling onto the flat feed-receiving plate 31 through a heating mesh of the heater 32 inside the housing of the combustion device 3. When the asphalt mixture completely falls on the flat feed-receiving plate 31, the slide block 282 moves back to the previously closed state, forming the closed structure inside the housing of the combustion device 3, which can effectively suppress the heat leakage inside the combustion device 3.

Inner walls on two sides of the housing of the combustion device 3 are fixed with hinges that are fixedly connected to the telescopic cylinders (not shown in the attached drawings, referring as to the telescopic cylinders 24 in FIG. 3). The telescopic cylinders are fixedly connected to the flat feed-receiving plate 31. The flat feed-receiving plate 31 is located below the heater 32 and is attached to the heating mesh of the heater 32. The heater 32 includes the heating mesh and a high-temperature insulation frame, and the heating mesh is fixedly connected inside the high-temperature insulation frame. Firstly, a combustion chamber of the combustion device 3 is preheated, namely that a temperature of the combustion chamber is raised to a required temperature for heating before the asphalt mixture enters the combustion chamber. Therefore, when the asphalt mixture enters, it can be immediately burned into an asphalt flue gas, achieving rapid measurement.

The asphalt flue gas enters the filter chamber 33 outside the combustion chamber through the through holes in the combustion device 3. The filter chamber 33 is equipped with an activated carbon filter mesh, and an exhaust vent 34 is opened on an outside of a back plate of the filter chamber 33. The asphalt flue gas passes through the activated carbon filter mesh, and harmful gases and smoke inside the asphalt flue gas are absorbed by the activated carbon filter mesh. Remaining gases in the asphalt flue gas are discharged into the air through the exhaust vent 34. The pulling sensors 9 outside the housing of the combustion device 3 also synchronously measures the weight of the asphalt mixture at each moment, and the weight change of the asphalt mixture can be reflected by the data change of the pulling sensors 9. The weighing process and combustion process are carried out simultaneously, which can improve the efficiency and accuracy of weighing. The pulling sensors 9 can timely transmit the data to the controller.

After the asphalt combustion is completed, the controller controls the movement of the telescopic cylinders to open the flat feed-receiving plate 31. The flat feed-receiving plate 31 is designed to be open towards opposite directions. After receiving instructions from the controller, the flat feed-receiving plate 31 is opened towards two opposite sides for feeding. A bottom of the combustion device 3 is equipped with a feeding hopper 29 of the combustion device 3, which has the same size as the inner chamber of the housing of the combustion device 3. An outlet (also referred as to a discharge port) of the feeding hopper 29 of the combustion device 3 is connected to the feed port of an upper cover 53 of the vibration screening device 5. After the asphalt combustion is completed, the obtained aggregates directly fall onto a layer of vibration sieve 54 through the feed port of the upper cover 53.

Figure 6:
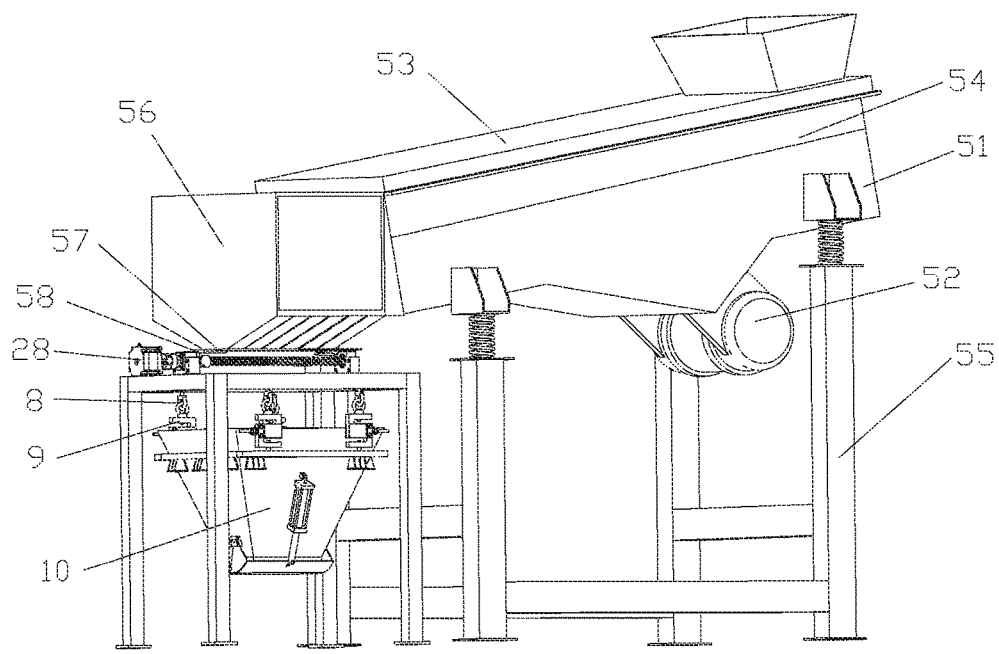
FIG. 6 illustrates a schematic structural diagram of a vibration screening device according to the embodiment of the disclosure.

As shown in FIG. 6, the vibration screening device 5 includes a box body 51, a vibration motor 52, the upper cover 53, multiple layers of vibration sieves 54, a base 55, multiple discharge ports 56 (i.e., corresponding to the multiple layers of vibration sieves 54), the weighing hopper 10, and other structures. The upper cover 53 is installed on the box body 51, the multiple layers of vibration sieves 54 are installed inside the box body 51, the vibration motor 52 is installed at a bottom of the box body 51, and the multiple discharge ports 56 are installed at a front end of the box body 51. The base 55 is fixed to the box body 51, and the weighing hopper 10 is correspondingly set at the lower portion of the multiple discharge ports 56. The weighing hopper 10 is fixedly connected to the base 55 by using corresponding pulling sensors 9 and corresponding suspension rods 8. A feed blocking door 57 is installed below the multiple discharge ports 56, and the feed blocking door 57 is fixedly connected to the slide block 282 of the ball screw slider assembly 28 through the fixed block 58.

The vibration screening device 5 is inclined with a certain angle, which aims to accelerate a falling speed of the aggregates and improve screening efficiency. Specially, the vibration screening device 5 is equipped with the multiple layers of vibration sieves 54 with different apertures, and the apertures of the vibration sieves 54 gradually decreases from a top to a bottom of the vibration screening device 5. Correspondingly, the screened particle sizes of the aggregates screened by the multiple layers of vibration sieves 54 gradually decreases from the top to the bottom of the vibration screening device 5. In an illustrated embodiment of the disclosure, according to gravity of the aggregates and large first and small later for the aggregates, the aggregates with the large particle sizes are first screened while the aggregates with the small particle sizes flow out from the vibration sieve 54 with the large aperture under the gravity. Therefore, the aggregates with minimum particle sizes are finally screened. Generally speaking, the aggregates are roughly graded, but proportions of the different particle sizes cannot be evaluated. However, the method according to the disclosure can solve the above problems. The vibration screening device 5 is driven by a driving mechanism such as two vibration motors 52. An eccentric block within the vibration motor 52 vibrates to drive the vibration sieves 54 and the aggregates to vibrate, thereby completing the screening of the aggregates. A movement trajectory of the aggregates is a parabolic forward motion and a trajectory of the parabolic forward motion for the aggregates has two movement directions, including: on the one hand, throwing the aggregates upwards, and on the other hand, making the aggregates move forward. An advantage of the parabolic trajectory compared to a linear trajectory is that it can improve the screening efficiency for the aggregates.

As mentioned above, the aggregates obtained after the asphalt combustion enters the vibration screening device 5 from the upper cover 53. Before the aggregates fall down, the vibration screening device 5 is opened. As soon as the aggregates fall on the multiple layers of vibration sieves 54, the aggregate screening begins. Under the driving force of the vibration motor 52, the aggregates move forward while being screened. After the aggregate screening, the aggregates with different particle sizes fall into the multiple discharge ports 56 disposed at ends of the multiple layers of vibration sieves 54. Due to the feed blocking door 57 disposed at the multiple discharge ports 56, the screened aggregates are stacked in a corresponding discharge port 56 corresponding to the layer of vibration sieve 54. After the aggregate screening is completed, the slide block 282 fixedly connected at the multiple discharge ports 56 starts to move, driving the feed blocking door 57 to open the multiple discharge ports 56 of the vibration screening device 5. Opening time of the multiple discharge ports 56 corresponding to different layers of vibration sieves 54 is different, and the multiple discharge ports 56 are opened in order from front to back. Between two adjacent discharge ports 56, it is necessary to wait for the aggregates in the previous discharge port 56 to completely fall onto the weighing hopper 10 before opening the next discharge port 56. In an illustrated embodiment of the disclosure, obtaining the aggregates after the asphalt combustion is as follows: opening the discharge port of the combustion device 3 and controlling the discharge port 56 of each layer of vibration sieve 54 to open while the discharge port of the combustion device 3 is opened.

When the aggregates in all of the discharge ports 56 fall onto the weighing hopper 10 in sequence, the pulling sensors 9 outside the weighing hopper 10 measure the weight of aggregates with different particle sizes. The weight change of the aggregates is reflected by the data change of the pulling sensors 9. After the weighing is completed, the pulling sensors 9 promptly transmit the data to the controller. Then, the controller controls the movement of telescopic cylinders to open a discharge door at the bottom of the weighing hopper 10. The discharge door of the weighing hopper 10 is designed to be open towards opposite directions. After receiving the command from the controller, the discharge door is opened towards the two opposite directions for feeding.

The embodiment of the disclosure integrates microwave dehydration, asphalt combustion, and aggregate screening, which can achieve automatic and rapid detection of the moisture content, the asphalt content, and the aggregate gradation of the asphalt mixture. It is of great significance for the regeneration of the waste asphalt mixture, thereby improving the efficiency of waste asphalt mixture, greatly alleviating the environmental pollution caused by waste asphalt mixture, and saving the use of raw materials with a positive development prospect.

As mentioned above, the embodiment of the automatic and rapid detection method of the gradation for the asphalt mixture includes the following steps:
asphalt mixture introduction, including: introducing the asphalt mixture by using a feeding mechanism;
asphalt mixture dehydration, including: heating the asphalt mixture in a heating device to remove moisture in the asphalt mixture and dehydrating the asphalt mixture to a target dehydration rate, thereby obtaining a dehydrated asphalt mixture;
asphalt combustion, including: burning the dehydrated asphalt mixture in a combustion device by using a combustion method to form smoke configured to be removed, thereby obtaining aggregates after the asphalt combustion, and obtaining an asphalt content by using a weight difference of the dehydrated asphalt mixture before and after the asphalt combustion;
aggregate screening, including: grading through screening the aggregates obtained after the asphalt combustion according to different particle sizes of the aggregates by using a vibration screening device, and then weighing the aggregates with the different particle sizes, thereby obtaining weights of the aggregates with the different particle sizes; and
obtaining the gradation, including: calculating the gradation for the asphalt mixture according to the weights of the aggregates with the different particle sizes and the asphalt content (e.g., weight proportions of the asphalt and the aggregates with the different particle sizes).

To facilitate a clearer understanding of the automatic and rapid detection method of the gradation for the asphalt mixture in the embodiment of the disclosure, the following puts forward an illustrated embodiment for brief explanation.

During the production process, an introduction device is used for introducing the asphalt mixture obtained by milling (referred as to a manner of scraping a layer of damaged pavement). For example, 500 grams (g) of milling asphalt mixture is taken, and then the asphalt mixture enters the heating device such as the microwave heating device 2 through the feeding mechanism 1.

The asphalt mixture falls on the arc-shaped feed-receiving plate 25 and then the asphalt mixture is dehydrated and dried by absorbing microwaves, and then the weighing system 4 outside the microwave heating device 2 weighs the asphalt mixture before and after the dehydration. The moisture content of the asphalt mixture is calculated based on the moisture content formula (specially the dried asphalt mixture not need to be further heated and dehydrated, and directly entering the next stage, i.e., asphalt combustion).

The dehydrated and dried asphalt mixture is fed into the combustion device 3 through the feeding hopper 29 of the microwave heating device 2, which is equipped with a heater 32, such as an electric heating element. After the dehydrated and dried asphalt mixture is dropped, it passes through the electric heating element and falls onto the flat feed-receiving plate 31. The flat feed-receiving plate 31 is attached to the electric heating element and is preheated before the dehydrated and dried asphalt mixture is dropped (i.e., the temperature inside the combustion device 3 reaching the required high-temperature environment).

After the dehydrated and dried asphalt mixture falls into the combustion device 3, the asphalt quickly burns in the high-temperature environment, turning into water and carbon dioxide. The substances after the asphalt combustion are then discharged outdoors through the filter chamber 33 and the toxic gases inside the substances are absorbed. Then, the weighing system 4 outside the combustion device 3 is used to weigh the asphalt mixture before and after the asphalt combustion, and the asphalt content of the asphalt mixture is calculated according to the formula.

The asphalt mixture obtained after the asphalt combustion is mineral aggregates (also referred as to aggregates), and the aggregates are fed into the vibration screening device 5 through the hopper 29 of the combustion device. The vibration screening device 5, for example, is a linear vibration screen machine with multiple layers of vibration sieves 54 installed inside. Driven by the vibration motor 52, the trajectory of the aggregates is a parabolic forward motion, and the aggregate screening is carried out simultaneously while moving forward. After the aggregate screening, the aggregates with various particle sizes accumulate at the multiple discharge ports 56 corresponding to the multiple layers of vibration sieves 54. There is a weighing hopper 10 disposed at the bottom of the multiple discharge ports 56, and the weighing hopper 10 faces directly each discharge port 56. There is a feed blocking door 57 disposed at the multiple discharge ports 56, which is driven by the ball screw slider assembly 28. The ball screw slider assembly 28 gradually drives the feed blocking door 57 to move, causing the aggregates with different particle sizes to gradually fall into the weighing hopper 10 and weigh the aggregates with each particle size, thus obtaining the aggregate gradation of the asphalt mixture.

The above embodiments are only used to illustrate the technical solutions of the disclosure and are not limited thereto. Although the disclosure has been described in detail with reference to the above embodiments, those skilled in the related art may still modify or replace the illustrated embodiments of the disclosure without departing from the spirit and scope of the disclosure. However, these modifications and replacements all fall within the scope of the protection of the disclosure.

What is claimed is:

1. An automatic detection method of a gradation for an asphalt mixture, comprising the following steps:
    asphalt mixture introduction, comprising: introducing the asphalt mixture;
    asphalt mixture dehydration, comprising: heating the asphalt mixture in a heating device to remove moisture in the asphalt mixture and dehydrating the asphalt mixture to a target dehydration rate, thereby obtaining a dehydrated asphalt mixture;
    asphalt combustion, comprising: burning the dehydrated asphalt mixture in a combustion device by using a combustion method to form smoke configured to be removed, thereby obtaining aggregates after the asphalt combustion, and obtaining an asphalt content by using a weight difference of the dehydrated asphalt mixture before and after the asphalt combustion;
    aggregate screening, comprising: grading through screening the aggregates obtained after the asphalt combustion according to different particle sizes of the aggregates by using a vibration screening device, and then weighing the aggregates with the different particle sizes, thereby obtaining weights of the aggregates with the different particle sizes; and
    obtaining the gradation, comprising: calculating the gradation for the asphalt mixture according to the weights of the aggregates with the different particle sizes and the asphalt content.

2. The method according to claim 1, wherein in the asphalt mixture dehydration, the asphalt mixture is heated to a temperature of 105 degrees Celsius (C) ±2° C. until the asphalt mixture is completely dehydrated.

3. The method according to claim 2, wherein in the asphalt mixture dehydration, the heating is performed by microwave heating configured to realize the asphalt mixture dehydration rapidly.

4. The method according to claim 1, wherein after the asphalt mixture dehydration, the method further comprises: collecting the dehydrated asphalt mixture, which is performed by gathering the dehydrated asphalt mixture into a feeding hopper, thereby gathering the dehydrated asphalt mixture into the feeding hopper.

5. The method according to claim 1, wherein in the asphalt combustion, the asphalt combustion is performed by a combustion furnace, and the combustion furnace is heated to a temperature of 520° C.-540° C.

6. The method according to claim 1, wherein in the aggregate screening, the vibration screening device is provided with a plurality of layers of vibration sieves therein from a top to a bottom of the vibration screening device; and screened particle sizes of the plurality of layers of vibration sieves are decreased from the top to the bottom of the vibration screening device.

7. The method according to claim 6, wherein a trajectory of the aggregates passing through the plurality of layers of vibration sieves is a parabolic motion under an action of a drive mechanism.

8. The method according to claim 6, wherein ends of the plurality of layers of vibration sieves of the vibration screening device are correspondingly provided with a plurality of discharge ports.

9. The method according to claim 8, wherein after the asphalt combustion, the method further comprises: discharging the aggregates after the asphalt combustion, which is performed by opening a discharge port of the combustion device according to a motion of the aggregates while controlling to open the plurality of discharge ports corresponding to the plurality of layers of vibration sieves in sequence.

10. The method according to claim 9, wherein in the asphalt combustion, after the dehydrated asphalt mixture enters a feed-receiving plate of the combustion device, an open-close cover plate of the combustion device is present in a closed state to form an asphalt sealing chamber.

\* \* \* \* \*